US009416408B2

(12) United States Patent
Robb (10) Patent No.: US 9,416,408 B2
(45) Date of Patent: Aug. 16, 2016

(54) **THERMOSTABILLIZATION OF DNA POLYMERASE BY PROTEIN FOLDING PATHWAY FROM A HYPERTHERMOPHILE ARCHAEON, *PYROCOCCUS FURIOSUS***

(75) Inventor: Frank T. Robb, Gaithersburg, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1964 days.

(21) Appl. No.: 12/065,152

(22) PCT Filed: Aug. 29, 2006

(86) PCT No.: PCT/US2006/034314
§ 371 (c)(1),
(2), (4) Date: Aug. 28, 2008

(87) PCT Pub. No.: WO2007/028069
PCT Pub. Date: Mar. 8, 2007

(65) Prior Publication Data
US 2008/0318281 A1    Dec. 25, 2008

Related U.S. Application Data

(60) Provisional application No. 60/712,149, filed on Aug. 29, 2005.

(51) Int. Cl.
*C12Q 1/68* (2006.01)

(52) U.S. Cl.
CPC ..................... *C12Q 1/686* (2013.01)

(58) Field of Classification Search
None
See application file for complete search history.

(56) References Cited

U.S. PATENT DOCUMENTS

| | | | |
|---|---|---|---|
| 5,474,892 | A | 12/1995 | Jakob et al. |
| 6,458,556 | B1 * | 10/2002 | Hayashizaki ............ 435/41 |
| 6,579,703 | B2 * | 6/2003 | Robb et al. ............ 435/91.1 |
| 2003/0233675 | A1 * | 12/2003 | Cao et al. ............ 800/279 |

OTHER PUBLICATIONS

Shockley et al. (Appl. Environ. Micro., 2003, 69(4):2365-2371).*
Maeder et al. (Genetics, 1999, 152:1299-1305).*
Vainberg et al. (Cell, 1998, vol. 93, p. 863-873).*
Hartl et al. (Science, 2002, 295(5561):1852-1858, IDS reference).*
Okochi et al. (Biochem. Biophys. Res. Comm, 2002, 291:769-774, IDS reference).*
Laksanalamai et al. (J. Bacteriol., 2001, 183(17):5198-5202).*
Macario et al. (Frontiers in Bioscience, 2004, vol. 9, p. 1318-1332).*
Barral, JM, Broadley SA: Schaffar C, Hard FU. 2004. Roles of molecular chaperones in protein misfolding diseases. *Semin Cell Dev Biol* 15(1);17-29.
Chang, Z, Primm, T P, Jakana J, Lee HI, Serysheva I, Chiu W, Gilbert HF, Quiocho FA. 1996. *Mycobacterium tuberculosis* 16-kDa antigen (Hsp16.3) functions as an oligomeric structure in vitro to suppress thermal aggregation *J Biol Chem.* 271(12):7218-23.
Dalton, R., 1999. Roche's Taq patent 'obtained by deceit', rules US court. *Nature* 402(6763):709.
Dalton, R., 2001. Patent ruling could cut PCR enzyme prices. *Nature* 411(6838):622.
Emmerhoff OJ, Klenk HP, Birkeland NK. 1998. Characterization and sequence comparison of temperature-regulated chaperonins from the hyperthermophilic archacon *Archaeoglobus fulgiaus. Gene* 215(2):43 1-8.
Haley DA, Bova MP, Huang QL, McHaourab HS, Stewart PL. 2000. Small heat-shock protein structures reveal a continuum from symmetric to variable assemblies. *J Mol Biol* 298(2):261-72.
Hartl FU. 1996. Molecular chaperones in cellular protein folding. *Nature* 381(6583)571-9.
Hartl, FU, Hayer-Hartl M. 2002. Molecular chaperones in the cytosol: from nascent chain to folded protein. *Science* 295(5561): 1852-8.
Kim KK, Kim R, Kim SH. 1998. Crystal structure of a small heal-shock protein. *Nature* 394(6693):595-9.
Klunker D, Haas B., Hirtreiter A, Figueiredo L, Naylor DJ, Pfeifer G, Muller V, Deppenmeier U, Gottschalk G, Hartl PU and others. 2003. Coexistence of group I and group II chaperonins in the archaeon *Methanosarcina mazei.* J Biol Chem 278(35) 3325&67.
Laksanalamai P., Macder DL, Robb PT. 2001 Regulation and mechanism of action of the small heat shock protein from the hyperthermophilic archaeon *Pyrococcus furiosus. J Bacteriol* 183(17);S198-202.
Laksanalamai P. Jiemjit A, Bu Z, Maeder DL, Robb FT. 2003. Multisubunit assembly of the *Pyrococcus furiosus* small heat shock protein is essential for cellular protection at high temperature. *Extremophlies* 7(1):79-83.
Laksanalamai P, Whitehead TA, Robb FT 2004. Minimal protein-folding systems in hyperthermophilic archaea. *Nat Rev Microbiol* 2(4);315-24.
Konicczny I, Liberek K. 2002. Cooperative action of *Escherichia coli* ClpB protein and DnaK chaperone in the activation of a replication initiation protein. *J. Biol Chem* (21):18483-8.
Nold SC, Ward DM. 1995. Diverse *Thermus* species inhabit a single hot spring microbial mat. *Syst Appl Microbiol* 18:274-8.
Okochi M, Matsuzaki H, Nomura T, Ishii N, Yohda M. 2005. Molecular characterization of the group II chaperonin from the hyperthermophilic archaeum *Pyrococcus horikoshii* OT3. *Extremophiles* 9(2):127-34.
Okochi M, Nomura T, Zako T, Arakawa T, Iizuka R, Ueda H., Funatsu T, Leroux M, Yohda M. 2004. Kinetics and binding sites for interaction of prefoldin with group II chaperonin: contiguous non-native substrate and chaperonin binding sites in archaeal prefoldin. *J Biol Chem.*
Okochi M, Yoshida T, Maruyama T, Kawarabayasi Y, Kikuchi H, Yohda M. 2002. Pyrococcus prefoldin stabilizes protein-folding intermediates and transfers them to chaperonins for correct folding. *Biochem Biophys Res Commun* 291(4):769-74.

(Continued)

*Primary Examiner* — Stephanie K Mummert
(74) *Attorney, Agent, or Firm* — Marianne Fuierer; Moore & Van Allen, PLLC (57) ABSTRACT

The present invention relates to maintaining the activity and stability of enzymes and biologically active proteins at increased temperatures by contacting same with a combination of isolated passive and active chaperones from a hyperthermopilic Archaeon, wherein the chaperones may include heat shock proteins, prefoldin and/or chaperonin proteins.

4 Claims, 3 Drawing Sheets

(56) References Cited

OTHER PUBLICATIONS

Pavlov AR, Belova GI Kozyavkin SA, Slesarev M. 2002. Helix-hairpin-helix motifs confer salt resistance and processivity on chimeric DNA polymerases. *Proc Natl Acad Sci U S A* 99(21): 13510-5.

Pavlov AR, Paviova NV, Kozyavkin SA, Slesarev A'. 2004. Recent developments in the optimization of thermostable DNA polymerases for efficient applications. *Trends Biotechnology* 22(s):253-60.

Robb PT, Maeder DL, Brown JR, DiRuggiero J, Stump MD, Yeh RK, Weiss RB, Dunn DM. 2001. Genomic sequence of hyperthermophile, *Pyrococcus furiosus*: implications for physiology and enzymology. *Methods Enzymol*. 330:134-57.

van Montfort RL, Basha E, Friedrich KL, Slingsby C, Vierling F. 2001. Crystal structure and assembly of a eukaryotic small heat shock protein. *Nat Struct Biol*. 8(12): 1025-30.

Veinger L, Diamant S, Buchner J, Goloibompff P. 1998. The small heat-shock protein IbpB from *Escherichia coli* stabilizes stress-denatured proteins for subsequent refolding by a multi chaperone network. *J Biol Chem* 273(18):1 1032-7.

Yon JM. 2001. Protein folding: a perspective for biology, medicine and biotechnology. *Braz J Med Biol Res* 34(4):419-35.

Young JC, Agashe VR, Siegers K, Hartl FU. 2004. Pathways of chaperone-mediated protein folding in the cytosol. *Nat Rev Mol Cell Biol* 5(10):781-91.

Nold SC, Ward DM. 1995 Diverse *Thermus* species inhabit a single hot spring microbial mat. *Syst Appl Microbiol* 18:274-8.

Laksanaiamai, Pongpan et al. Stabilization of *Taq* DNA Polymerase at High Temperature by Protein Folding Pathways From a Hyperthermophilic Archaeon, *Pyrococcus furiosus*. Biotechnology and Bioengineering, 93(1), Jan. 5, 2005.

Shockley et al. Heat Shock Response by the Hyperthermophilic Archaeon (*Pyrococcus furiosus*). Applied and Environmental Microbiology, Apr. 2003, vol. 69, No. 4, pp. 2365-2371.

Lee, Yuh-Ru Julie, Nagao, Ronald T., Lin, chu Yung and Key, Joe L. 1996. Induction and Regulation of Heat Shock Gene Expression by an Amino Acid Analog in Soybean Seedlings. Plant Physiol. 110:241-48.

Almoguera, Concepclon, Coca, Maria A. and Jorando, Juan 1993. Tissue-specific expression of sunflower heat shock proteins in response to water stress. The Plant Journal 4(6), pp. 947-958.

Almoguera, Concepclon and Jordano, Juan 1992. Developmental and environmental concurrent expression of sunflower dry-seed-stored low-molecular-weight heat shock protein and Lea mRNAs. Plant Molecular Biology 19:781-792.

Apuya, Nestor R. and Zimmerman, J. Lynn. 1992. Heat Shock Gene Expression Is Controlled Primarily at the Translational Level in Carrot Cells and Somatic Embyos. The Plant Cell, vol. 4, pp. 657-665.

Zimmerman, J. Lynn, Apuya, Nestor, Darwish, Kamel and O'Carroll, Cynthia 1989. Novel Regulation of Heat Shock Genes during Carrot Somatic Embryo Development. The Plant Cell, vol. 1, pp. 1137-1146.

Kim, Rosalind, Kim, Kyeong Kyu, Yokota, Hisao and Kim, Sung Hou. 1998. Small heat shock protein of *Methanococcus jannaschii*, a hyperthermophile. Proc. Natl. Acad. Sci USA, vol. 95, pp. 9129-9133.

Gonzalez, Juan M., Masuchi, Yaeko, Robb, Frank T., Ammerman, James W., Maeder, Dennis L., Yanagibayashi, Miki, Tamaoka, Jin and Kato, Chiaki. 1998. *Pyrococcus horikoshii* sp. Nov.; a hyperthermophilic archaeon isolated from a hydrothermal vent at the Okinawa Trough. Extremophiles, 2:123-130.

Adams, M.W.W. 1995. Large-scale growth of Hyperthermophiles. Archaea, A Laboratory Manual, Thermphiles pp. 47-49.

Database Genbank, Asccession No. GI 7963823. Laksanalamai, P. et al., *Pyrococcus furiosus* small heat shock protein gene, Complete eds. Aug. 12, 2001.

Zietara, M.S. and Skorkowski. 1995. Thermostability of Lactate Dehydrogenase LDH-A Isoenzyme: Effect of Heat Shock Protien DnaK on the Enzyme Activity. Int. J. Biochem. Cell Biol. vol. 1169-1174.

Yeh, C-H. 1997. Expression of a gene encoding a 16.9-kDa heat shock protein, Pshsp 16.9, in *Escherichia coli* enhances thermotolerance. Proc. Natl. Acad. Sci. U.S.A. vol. 94, pp. 10967-10972.

Robb. Evidence for a versatile chaperone and protein degradation functions in hyperthermopilic archaea, Abstract for 229th ACS National Meeting in San Diego, public availability on Jan. 10, 2005.

* cited by examiner

SEQUENCE LISTING

```
<160> NUMBER OF SEQ ID NOS: 14

<210> SEQ ID NO 1
<211> LENGTH: 167
<212> TYPE: PRT
<213> ORGANISM: Pyrococcus furiosus

<400> SEQUENCE: 1

Met Val Arg Arg Ile Arg Arg Trp Asp Ile Trp Asp Pro Phe Asp Leu
1               5                   10                  15

Ile Arg Glu Ile Gln Glu Glu Ile Asp Ala Met Phe Asp Glu Phe Phe
            20                  25                  30

Ser Arg Pro Arg Leu Trp Thr Tyr Arg Arg Trp Ser Glu Pro Ala Met
        35                  40                  45

Tyr Glu Glu Arg Val Gly Glu Val Trp Arg Glu Pro Phe Val Asp Ile
    50                  55                  60

Phe Asp Asn Gly Asp Glu Phe Val Ile Thr Ala Glu Leu Pro Gly Val
65                  70                  75                  80

Arg Lys Glu Asp Ile Lys Val Arg Val Thr Glu Asp Thr Val Tyr Ile
                85                  90                  95

Glu Ala Thr Val Lys Arg Glu Lys Glu Leu Glu Arg Glu Gly Ala Val
            100                 105                 110

Arg Ile Glu Arg Tyr Phe Thr Gly Tyr Arg Arg Ala Ile Arg Leu Pro
        115                 120                 125

Glu Glu Val Ile Pro Glu Lys Ala Lys Ala Lys Tyr Asn Asn Gly Val
    130                 135                 140
```

```
Leu Glu Ile Arg Val Pro Lys Lys His Pro Thr Lys Lys Glu Ser Glu
145                 150                 155                 160

Gly Phe Glu Val Lys Val Glu
                165

<210> SEQ ID NO 2
<211> LENGTH: 156
<212> TYPE: PRT
<213> ORGANISM: Pyrococcus furiosus

<400> SEQUENCE: 2

Met Val Arg Arg Ile Arg Arg Trp Asp Ile Trp Asp Pro Phe Asp Leu
1               5                   10                  15

Ile Arg Glu Ile Gln Glu Glu Ile Asp Ala Met Phe Asp Glu Phe Phe
                20                  25                  30

Ser Arg Pro Arg Leu Trp Thr Tyr Arg Arg Trp Ser Glu Pro Ala Met
            35                  40                  45

Tyr Glu Glu Arg Val Gly Glu Val Trp Arg Glu Pro Phe Val Asp Ile
        50                  55                  60

Phe Asp Asn Gly Asp Glu Phe Val Ile Thr Ala Glu Leu Pro Gly Val
65                  70                  75                  80

Arg Lys Glu Asp Ile Lys Val Arg Val Thr Glu Asp Thr Val Tyr Ile
                85                  90                  95

Glu Ala Thr Val Lys Arg Glu Lys Glu Leu Glu Arg Glu Gly Ala Val
            100                 105                 110

Arg Ile Glu Arg Tyr Phe Thr Gly Tyr Arg Arg Ala Ile Arg Leu Pro
        115                 120                 125

Glu Glu Val Ile Pro Glu Lys Ala Lys Ala Lys Tyr Asn Asn Gly Val
    130                 135                 140

Leu Glu Ile Arg Val Pro Lys Lys His Pro Thr Lys
145                 150                 155

<210> SEQ ID NO 3
<211> LENGTH: 146
<212> TYPE: PRT
<213> ORGANISM: Pyrococcus furiosus

<400> SEQUENCE: 3

Met Glu Asn Asn Lys Glu Leu Glu Lys Val Ala Tyr Glu Tyr Gln Val
1               5                   10                  15

Val Gln Ala Gln Ala Gln Leu Leu Ala Gln Asn Leu Glu Leu Leu Ser
                20                  25                  30

Leu Ala Gln Ala Glu Val Gln Thr Val Lys Glu Thr Leu Glu Asn Leu
            35                  40                  45

Met Lys Ile Glu Asp Glu Asn Pro Glu Ile Leu Val Pro Ile Gly Ala
        50                  55                  60

Gly Ser Phe Leu Lys Gly Lys Ile Val Asp Lys Asn Asn Ala Ile Ile
65                  70                  75                  80

Ser Val Gly Ser Gly Tyr Ala Val Glu Lys Thr Leu Glu Asp Ala Ile
                85                  90                  95

Lys Tyr Leu Asp Glu Arg Ile Lys Glu Tyr Asp Glu Ala Ile Arg Lys
            100                 105                 110

Thr Gln Glu Ala Leu Asn Glu Leu Gln Lys Arg Ala Ala Glu Leu Ala
        115                 120                 125
```

```
Lys Lys Ala Gln Glu Ile Gln Lys Gln Ala Met Ser Phe Lys Leu
    130                 135                 140

Lys Lys
145
```

<210> SEQ ID NO 4
<211> LENGTH: 117
<212> TYPE: PRT
<213> ORGANISM: Pyrococcus furiosus

<400> SEQUENCE: 4

```
Met Gln Asn Ile Pro Pro Gln Val Gln Ala Met Leu Gly Gln Leu Glu
1               5                   10                  15

Ser Tyr Gln Gln Gln Leu Gln Leu Val Ile Gln Gln Lys Gln Lys Val
            20                  25                  30

Gln Ala Asp Leu Asn Glu Ala Lys Lys Ala Leu Glu Glu Ile Glu Lys
        35                  40                  45

Leu Thr Asp Asp Ala Val Ile Tyr Lys Thr Val Gly Thr Leu Ile Val
50                  55                  60

Lys Thr Thr Lys Glu Lys Ala Leu Gln Glu Leu Lys Glu Lys Val Glu
65                  70                  75                  80

Thr Leu Glu Val Arg Leu Asn Ala Leu Asn Arg Gln Glu Gln Lys Ile
                85                  90                  95

Asn Glu Lys Ile Lys Glu Leu Thr Gln Lys Ile Gln Ala Ala Leu Arg
            100                 105                 110

Pro Pro Thr Ala Gly
        115
```

<210> SEQ ID NO 5
<211> LENGTH: 549
<212> TYPE: PRT
<213> ORGANISM: Pyrococcus furiosus

<400> SEQUENCE: 5

```
Met Ala Gln Leu Ala Gly Gln Pro Ile Leu Ile Leu Pro Glu Gly Thr
1               5                   10                  15

Gln Arg Tyr Val Gly Arg Asp Ala Gln Arg Met Asn Ile Leu Ala Ala
            20                  25                  30

Arg Ile Val Ala Glu Thr Ile Arg Thr Thr Leu Gly Pro Lys Gly Met
        35                  40                  45

Asp Lys Met Leu Val Asp Ser Leu Gly Asp Ile Val Ile Thr Asn Asp
    50                  55                  60

Gly Ala Thr Ile Leu Asp Glu Met Asp Ile Gln His Pro Ala Ala Lys
65                  70                  75                  80

Met Met Val Glu Val Ala Lys Thr Gln Asp Lys Glu Ala Gly Asp Gly
                85                  90                  95

Thr Thr Thr Ala Val Val Ile Ala Gly Glu Leu Leu Arg Lys Ala Glu
            100                 105                 110

Glu Leu Leu Asp Gln Asn Ile His Pro Ser Ile Ile Lys Gly Tyr
        115                 120                 125

Thr Leu Ala Ala Gln Lys Ala Gln Glu Ile Leu Glu Asn Ile Ala Lys
    130                 135                 140

Glu Val Lys Pro Asp Asp Glu Glu Ile Leu Leu Lys Ala Ala Met Thr
145                 150                 155                 160

Ser Ile Thr Gly Lys Ala Ala Glu Glu Glu Arg Glu Tyr Leu Ala Lys
                165                 170                 175
```

Leu Ala Val Glu Ala Val Lys Leu Val Ala Glu Lys Glu Asp Gly Lys
            180                 185                 190

Tyr Lys Val Asp Ile Asp Asn Ile Lys Leu Glu Lys Lys Glu Gly Gly
        195                 200                 205

Ser Val Arg Asp Thr Gln Leu Ile Arg Gly Val Val Ile Asp Lys Glu
    210                 215                 220

Val Val His Pro Gly Met Pro Lys Arg Val Glu Lys Ala Lys Ile Ala
225                 230                 235                 240

Leu Ile Asn Asp Ala Leu Glu Val Lys Glu Thr Glu Thr Asp Ala Glu
                245                 250                 255

Ile Arg Ile Thr Ser Pro Glu Gln Leu Gln Ala Phe Leu Glu Gln Glu
            260                 265                 270

Glu Arg Met Leu Arg Glu Met Val Glu Lys Ile Lys Glu Val Gly Ala
        275                 280                 285

Asn Val Val Phe Val Gln Lys Gly Ile Asp Asp Leu Ala Gln His Tyr
    290                 295                 300

Leu Ala Lys Tyr Gly Ile Met Ala Val Arg Arg Val Lys Lys Ser Asp
305                 310                 315                 320

Met Glu Lys Leu Ala Lys Ala Thr Gly Ala Lys Ile Val Thr Asn Ile
                325                 330                 335

Arg Asp Leu Thr Pro Glu Asp Leu Gly Tyr Ala Glu Leu Val Glu Glu
            340                 345                 350

Arg Lys Val Ala Gly Glu Ser Met Ile Phe Val Glu Gly Cys Gln Asn
        355                 360                 365

Pro Lys Ala Val Thr Ile Leu Ile Arg Gly Gly Thr Glu His Val Val
    370                 375                 380

Asp Glu Val Glu Arg Ala Leu Glu Asp Ala Ile Lys Val Val Lys Asp
385                 390                 395                 400

Ile Leu Glu Asp Gly Lys Ile Leu Ala Gly Gly Ala Pro Glu Ile
                405                 410                 415

Glu Leu Ala Ile Arg Leu Asp Glu Tyr Ala Lys Glu Val Gly Gly Lys
            420                 425                 430

Glu Gln Leu Ala Ile Glu Ala Phe Ala Glu Ala Leu Lys Val Ile Pro
        435                 440                 445

Arg Thr Leu Ala Glu Asn Ala Gly Leu Asp Pro Ile Glu Thr Leu Val
    450                 455                 460

Lys Val Ile Ala Ala His Lys Glu Lys Gly Pro Thr Ile Gly Val Asp
465                 470                 475                 480

Val Tyr Glu Gly Glu Pro Ala Asp Met Leu Glu Arg Gly Val Ile Glu
                485                 490                 495

Pro Leu Arg Val Lys Lys Gln Ala Ile Lys Ser Ala Ser Glu Ala Ala
            500                 505                 510

Ile Met Ile Leu Arg Ile Asp Asp Val Ile Ala Ala Ser Lys Leu Glu
        515                 520                 525

Lys Glu Lys Glu Lys Glu Gly Glu Lys Gly Gly Gly Ser Glu Asp Phe
    530                 535                 540

Ser Ser Asp Leu Asp
545

<210> SEQ ID NO 6
<211> LENGTH: 37
<212> TYPE: DNA
<213> ORGANISM: Artificial Sequence
<220> FEATURE:
<223> OTHER INFORMATION: Synthetic construct

<400> SEQUENCE: 6
ccatatggaa aacaataagg aattggaaaa ggttgct　　　　　　　　　　　　37

<210> SEQ ID NO 7
<211> LENGTH: 37
<212> TYPE: DNA
<213> ORGANISM: Artificial Sequence
<220> FEATURE:
<223> OTHER INFORMATION: Synthetic Construct

<400> SEQUENCE: 7
cctcgagtca cttcttaagc ttgaagctca ttgcttg　　　　　　　　　　　　37

<210> SEQ ID NO 8
<211> LENGTH: 36
<212> TYPE: DNA
<213> ORGANISM: Artificial Sequence
<220> FEATURE:
<223> OTHER INFORMATION: Synthetic Construct

<400> SEQUENCE: 8
ccatatgaat cccagggtgt gccaagtgga tttagg　　　　　　　　　　　　　36

<210> SEQ ID NO 9
<211> LENGTH: 44
<212> TYPE: DNA
<213> ORGANISM: Artificial Sequence
<220> FEATURE:
<223> OTHER INFORMATION: Synthetic Construct

<400> SEQUENCE: 9
cctcgagtca tccagcggtt ggaggtctta gggctgcctg aatc　　　　　　　　44

<210> SEQ ID NO 10
<211> LENGTH: 712
<212> TYPE: DNA
<213> ORGANISM: Pyrococcus furiosus

<400> SEQUENCE: 10 tctttttttgg agtattttttg attgttcggt aaattctact cttatcgaaa atatttataa    60
accccaaata atttaataac taatggtaac caaaagtggg aggggtgag agagatggtg    120
aggagaataa gaagatggga catatgggat ccattcgacc taataaggga aatacaagag    180
gaaattgatg caatgttcga tgaattcttc agcaggccaa ggctctggac ttacagaagg    240
tggagcgagc cagcaatgta tgaggagaga gtaggagaag tctggagaga gccattcgtt    300
gatatctttg acaacggaga tgagtttgta atcacggcag agcttccagg agtgagaaaa    360
gaagacatca aagtgagggt tacagaggat acagtataca ttgaggccac agttaagagg    420
gagaaagaat tagaaagaga aggagcagtg agaatagaga gatactttac agggtataga    480
agagccatca ggcttccaga agaagttatt ccagagaagg caaaggccaa gtacaacaac    540
ggagtgcttg agatcagagt tccaaagaag cacccaacaa agaaggagag tgaaggattc    600
gaagttaaag ttgaatagct ttagtaccct tctttcttga ttatttggaa atattttttgg    660
aggtattggt tctattatca attaattcct tttattttaa aatccttgga tc           712

<210> SEQ ID NO 11
<211> LENGTH: 468
<212> TYPE: DNA
<213> ORGANISM: Pyrococcus furiosus

<400> SEQUENCE: 11

```
atggtgagga gaataagaag atgggacata tgggatccat tcgacctaat aagggaaata    60
caagaggaaa ttgatgcaat gttcgatgaa ttcttcagca ggccaaggct ctggacttac   120
agaaggtgga gcgagccagc aatgtatgag gagagagtag gagaagtctg gagagagcca   180
ttcgttgata tctttgacaa cggagatgag tttgtaatca cggcagagct tccaggagtg   240
agaaaagaag acatcaaagt gagggttaca gaggatacag tatacattga ggccacagtt   300
aagagggaga aagaattaga aagagaagga gcagtgagaa tagagagata ctttacaggg   360
tatagaagag ccatcaggct tccagaagaa gttattccag agaaggcaaa ggccaagtac   420
aacaacggag tgcttgagat cagagttcca aagaagcacc caacaaag              468
```

<210> SEQ ID NO 12
<211> LENGTH: 1650
<212> TYPE: DNA
<213> ORGANISM: Pyrococcus furiosus

<400> SEQUENCE: 12

```
atggcccagt tagcaggcca acccattcta attttgcctg aaggaaccca agatacgtt     60
ggtagagatg cccagagaat gaacattctt gctgctagaa ttgttgcaga gacaataaga   120
acaaccctcg gaccaagggg aatggacaag atgctcgttg atagccttgg agacatcgta   180
ataacaaacg acggtgcaac aattctcgat gagatggaca ttcagcaccc agcagctaag   240
atgatggttg aggtcgcaaa gacccaggac aaggaggccg gtgatggaac aacaaccgct   300
gtagtaattg caggtgagct cctaagaaag gctgaagaat tactagacca gaacattcac   360
ccaagcataa tcatcaaagg ttacacccta gcagcacaaa aggctcaaga gatcctcgag   420
aacatagcca agaagtcaa gcccgacgat gaggaaattc tcctcaaggc tgcaatgaca   480
tcaattaccg gtaaggccgc tgaggaggag agggagtact tagccaagct tgcagtagag   540
gcagttaagc tagttgcaga gaaggaagac ggaaagtaca aggttgacat cgacaacatc   600
aagctcgaga gaaggagggg tggaagcgtc agagacaccc agctcataag aggtgtagtt   660
attgacaagg aagtagtcca cccaggaatg ccaaagagag tcgagaaagc taagattgca   720
ctaattaacg atgcacttga ggttaaggag accgagactg atgccgagat aagaattacc   780
agcccagagc aactccaggc cttcctcgag caagaggaga gaatgctcag agagatggtc   840
gagaagatca aggaagtcgg agctaacgta gtattcgtcc agaagggaat tgacgatcta   900
gcacagcact acctagccaa atacggaata atggccgtca gaagagtcaa gaagagcgac   960
atggagaagc tcgccaaggc cacaggagct aagatcgtaa ccaacattag ggacctcaca  1020
ccagaggacc tcggttacgc tgagctagta aagagagaa aggttgctgg agagagcatg  1080
atattcgtcg agggctgcca gaaccccaag gctgtgacaa tcctcatcag aggtggaact  1140
gagcacgtag tcgatgaggt cgagagagcc ctagaagatg caataaaggt tgtgaaggac  1200
atccttgaag atggaaagat cctagctggc ggtggagcac cagaaatcga gttagccatt  1260
agactcgacg agtacgccaa ggaagttggt ggcaaggagc agttggcaat tgaggccttt  1320
gcagaggctc tcaaggtcat tccaaggaca ctagcagaga acgctggtct cgacccaatc  1380
gagacactcg ttaaggtcat cgctgcccac aaggagaagg gaccaaccat cggtgtcgat  1440
gtatacgaag cgaaccagc agacatgcta gagagaggag tcatcgagcc actaagagtc  1500
aagaagcaag ctatcaagag tgctagcgag gcagcaataa tgatcctcag aatcgacgat  1560
```

```
gtcatcgctg ccagcaagct cgagaaagag aaggagaaag aaggtgagaa gggaggagga      1620
agcgaggact tcagcagtga tctagactga                                       1650

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
gtaatacgac tcactatagg g                                                21

<210> SEQ ID NO 14
<211> LENGTH: 31
<212> TYPE: DNA
<213> ORGANISM: Artificial Sequence
<220> FEATURE:
<223> OTHER INFORMATION: Synthetic Construct

<400> SEQUENCE: 14
cattatgctg agtgatatcc caaaaacccc c                                     31
```

THERMOSTABILLIZATION OF DNA POLYMERASE BY PROTEIN FOLDING PATHWAY FROM A HYPERTHERMOPHILE ARCHAEON, *PYROCOCCUS FURIOSUS*

CROSS-REFERENCE TO RELATED APPLICATION

The present application claims priority to PCT Application No. PCT/US2006/034314 filed in the U.S. Patent and Trademark Office, PCT Division, on Aug. 29, 2006, which in turn claims priority to U.S. Provisional Patent Application No. 60/712,149 filed on Aug. 29, 2005, the contents of all applications are hereby incorporated by reference herein.

GOVERNMENT RIGHTS IN INVENTION

This invention was made with government support under Grant Number GM073295 awarded by the National Institutes of Health. The government has certain rights in the invention.

BACKGROUND OF THE INVENTION

1. Field of the Invention

The present invention relates to maintaining the activity of enzymes, and more specifically to a combination of protein chaperones from a hyperthermopilic Archaeon for extending the durability and activity of an enzyme.

2. Description of the Related Art

Hyperthermophiles are defined as microorganisms that grow optimally at or above 80° C. Their high temperature resistance raises questions regarding the protein chaperones that can fold proteins at very high temperatures. In common with other hyperthermophiles, *Pyrococcus furiosus*, an archaeon that grows optimally at 100° C., encodes a reduced set of protein chaperones compared with eukaryotes or Archaea with lower growth temperatures (Laksanalamai et al. 2004). In the *P. furoisus* genome (Robb et al. 2001), two chaperones, the small heat shock protein (sHsp) and the sHsp60 (chaperonin), have been annotated, expressed and characterized. In addition, several putative chaperones, such as prefoldin, HtpX and Nascent peptide Associated Complex (NAC) have been identified (Laksanalamai et al. 2004). The most extensively studied chaperone in *P. furiosus* is the sHsp, which is an alpha-crystallin homolog with conserved sequence motifs in common with sHsps and crystallins from all domains of life (Chang et al. 1996; Haley et al. 2000; Kim et al. 1998; Laksanalamai et al. 2003; Laksanalamai et al. 2001; van Montfort et al. 2001). Several lines of evidence indicate that sHsps can prevent denatured proteins from aggregating but are unable to refold non-native proteins in a catalytic fashion (Chang et al. 1996; Laksanalamai et al. 2001). Hsp60s on the other hand catalyze ATP-dependent protein folding (Hartl 1996; Hartl and Hayer-Hartl 2002).

The heat shock proteins of the invention, *Pyrococcus furiosus* (sHSP), confer thermotolerance on cellular cultures and on proteins in cellular extracts during prolonged incubation at elevated temperature, demonstrating the ability to protect cellular proteins and maintain cellular viability under heat stress conditions. Such heat shock proteins are effective to combat enzymatic aggregation and intracellular precipitation during heat stress, and thereby enable enhancement of the utility and stability of enzymes in various applications, such as use of Taq polymerase in polymerase chain reaction (PCR) applications, digestive enzymes in microbial degradative applications, etc.

The PCR is a powerful method for the rapid and exponential amplification of target nucleic acid sequences. PCR has facilitated the development of gene characterization and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers.

An important modification of the original PCR technique was the substitution of *Thermus aquaticus* (Taq) DNA polymerase in place of the Klenow fragment of *E. coli* DNA pol I. The incorporation of a thermostable DNA polymerase into the PCR protocol obviates the need for repeated enzyme additions and permits elevated annealing and primer extension temperatures which enhance the specificity of primer:template associations. Taq polymerase thus serves to increase the specificity and simplicity of PCR.

However, while the heat shock proteins provides stability of DNA polymerases in high heat conditions, there is a need in the art to provide a composition that has the potential to promote refolding of proteins and assembly for reuse of polymerases, such as the Taq polymerase.

SUMMARY OF THE INVENTION

In one aspect, the present invention relates to a composition comprising isolated chaperones from a hyperthermophilic archaeon for enhancing the solubility and stability of proteins/enzymes at increased temperature and further providing for folding of native and non-native proteins in a catalytic fashion.

In another aspect, the present invention relates to a composition comprising isolated chaperones from *Pyrococcus furiosus* including at least a small heat shock protein (sHsp), a prefoldin (Pfd) and a chaperonin (Cpn)(hsp60) in an amount to enhance the stability of DNA polymerase during functional enzyme-driven processes such as PCR.

In a further aspect, the present invention relates to a composition comprising an isolated sHsp and/or beta subunit of prefoldin in combination with an isolated Hsp60, to improve the thermostability of Taq polymerase in a PCR reaction.

In a still further aspect the present invention relates to a composition comprising a small heat shock protein (SEQ ID NO: 1), a truncated version thereof (SEQ ID NO: 2) or a homologous sequence have at least 90%, 95% or 99% homology thereof; a subunit of prefoldin including either α (SEQ ID NO: 3), β (SEQ ID NO: 4), a combination of both, or a homologous sequence have at least 90%, 95% or 99% homology thereof; and a chaperonin (SEQ ID NO: 5) or a homologous sequence have at least 90%, 95% or 99% homology thereof.

In yet another aspect, the present invention relates to a method of synthesizing or amplifying at least one nucleic acid molecule, said method comprising;

(a) combining, in a mixture, at least one nucleic acid template, at least one polymerase, and a heat shock protein and/or prefoldin subunit in combination with sHsp60; and (b) incubating said mixture under conditions sufficient to make one or more first nucleic acid molecules complementary to all or a portion of said nucleic acid template.

Another aspect of the present invention relates to a method of protecting and extending the durability of a recombinant DNA polymerase or other enzyme used in a PCR amplification, comprising the steps of:
a) isolating a heat shock protein, perfoldin and sHsp60 from *P. furiosus*;
b) adding the heat shock protein and/or prefoldin in combination with sHsp60 to a buffer solution containing the DNA polymerase or other enzyme;
c) incubating the solution at extended temperature for extended time;
d) adding components necessary for PCR;
e) thermocycling the reaction to produce product from amplification of genomic deoxyribonucleic acid; and
f) examining the product of the reaction by gel electrophoresis.

Yet another aspect of the invention relates to a method of enhancing the thermostability of Taq polymerase and protein folding activity at elevated temperatures and during thermal recycling, the method comprising
adding a low molecular weight heat shock protein and/or perfoldin in combination with sHSP60 of *P. furiosus* to the solution;
elevating the temperature of the solution; and
measuring the enzymatic activity of Taq polymerase by absorbance.

A still further aspect of the invention relates to a PCR kit comprising a composition comprising passive and active chaperones of *P. furiosus*, including a heat shock protein and/or perfoldin in combination with sHPS60, and one or more other PCR reagents.

In a further compositional aspect, the invention relates to a composition comprising:
(i) a biological component; and
(ii) a composition comprising a *P. furiosus* Hsp, *P. furiosus* sHsp60 and at least on *P. furiosus* subunit of prefoldin or a precursor thereof, that are
(A) exogenous to the biological component, and
(B) thermostabilizingly effective for the biological component in the composition.

Other aspects, features and embodiments of the invention will be more fully apparent from the ensuing disclosure and appended claims.

DETAILED DESCRIPTION AND PREFERRED EMBODIMENTS OF THE INVENTION

The present invention relates to maintaining the activity of proteins, and more specifically to a combination of three protein chaperones, a small heat shock protein (sHsp), a prefoldin (Pfd) and a chaperonin (Cpn) from *Pyrococcus furiosus* wherein the passive chaperones sHsp and/or Pfd from *P. furiosus* can boost the protein refolding activity of Cpn for extending the durability of a recombinant DNA polymerase, such as Taq polymerase.

Definitions

As used herein, the following terms have the following meanings.

As used herein, the terms "heat shock protein" and "truncated heat shock protein" refer to any protein whose synthesis is enhanced when an organism or its cells are exposed to an increased temperature for that species; typically a temperature increase in a range of from about 5 to about 15° C.

As used herein, the term "low molecular weight heat shock protein" refers to those heat shock proteins that are between 12-42 kilodaltons (kDa) in size.

As used herein, the term "thermotolerance" refers to the ability of a cell to survive exposure to temperatures above its normal growth temperature.

As used herein, the term "DNA molecule" refers to the polymeric form of deoxyribonucleotides (adenine, guanine, thymine or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids and chromosomes.

As used herein, the term "transgenic cell line" or "transgenic culture" refers to a cell or culture that has stably incorporated added DNA sequences into its genome after deliberate introduction of DNA into that cell.

As used herein, the term "vector" refers to a replicon, such as a plasmid, phage, cosmid or virus to which another DNA or RNA segment may be attached to bring about the replication of the attached segment. Specialized vectors were used herein, containing various promoters, polyadenylation signals, genes for selection, etc.

As used herein, the term "transcriptional and translational control sequences" refer to DNA regulatory sequences, such as promoters, enhancers, polyadenylation signals, terminators, and the like, that provide for the expression of a coding sequence in a host cell.

As used herein, the term "promoter sequence" is a DNA regulatory region capable of binding RNA polymerase in a cell and initiating transcription of a downstream (3' direction) coding sequence. Eukaryotic promoters will often, but not always, contain "TATA" boxes and "CAT" boxes. Prokaryotic promoters contain Shine-Dalgarno sequences in addition to the −10 and −35 consensus sequences.

As used herein, the term "selection gene" refers to a gene that enables the discrimination of cells displaying a required phenotype upon implementation of certain conditions. For example, the growth of bacteria in a medium containing antibiotics to select for the bacterial cells containing antibiotic resistance genes.

As used herein, the terms "restriction endonucleases" and "restriction enzymes" refer to bacterial enzymes, each of which cuts double-stranded DNA at or near a specific nucleotide sequence.

As used herein, the terms "transformed" or "transfected" by exogenous or heterogeneous DNA when such DNA has been introduced inside the cell. The transforming DNA may or may not be integrated (covalently linked) into the genome of the cell. In prokaryotes, yeast and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones of a population of daughter cells containing the transforming DNA.

As used herein, the term "cell line" is a clone of a primary cell that is capable of stable growth in vitro for many generations.

As used herein, the term "isolated" refers to material is removed from its original environment (e g. the natural environment where the material is naturally occurring). For example, a polynucleotide or polypeptide while present in a living organism is not isolated, but the same polynucleotide or polypeptide, which is separated from some or all of the coexisting materials in the natural system, is isolated. Such polynucleotides could be part of a vector and/or such polynucleotides or polypeptides could be part of a composition, and still be isolated in that the vector or composition and is not part of the natural environment.

As used herein, the term "nucleic acid sequence" refers to an oligonucleotide, nucleotide, or polynucleotide, and fragments or portions thereof, and to DNA, cDNA or RNA of genomic or synthetic origin, which may be single- or double-stranded, and represent the sense or antisense strand.

As used herein, the term "amino acid sequence" refers to an oligopeptide, peptide, polypeptide, or protein sequence, and fragments or portions thereof, and to naturally occurring or synthetic molecules.

As used herein, the term "homologous" refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the biological and functional activity as the sequence to which it is homologous. As used herein, "substantially homologous" as used herein means that a sequence is at least 75% identical, and preferably at least 95% and more preferably 98% homology to the reference peptide. The sequence may differ by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical nucleic acid sequence "codes for a substantially identical amino acid sequence as defined above.

In accordance with the present invention, conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells & Enzymes," IRL Press (1986); "A Practical Guide to Molecular Cloning," B. Perbal (1984).

The invention contemplates enhancing the stability of Taq polymerase in a PCR operation, by conducting the PCR operation in the presence of both active and passive chaperones from *P. furiosus*. The PCR operation may be carried out with the provision of a PCR kit including PCR primers, Taq polymerase, deoxyribonucleoside triphosphates and the three chaperons n HSP according to the present invention.

Transformed cells capable of expressing the chaperones of *P. furiosus* may be readily formed and utilized to produce the proteins for various applications of the invention, e.g., by use of recombinant DNA vectors for expression of the three chaperones.

The small heat shock protein from *Pyrococcus furiosus* (Pfu-sHSP) is composed of 167 amino acid residues encoded by an ORF of 504 nucleotides (GenBank Accession number AF256212). A truncated heat shock protein from *Pyrococcus furiosus* (Pfu-tsHSP) is composed of 156 amino acid residues encoded by a truncated ORF of 471 nucleotides (including a stop codon).

The invention is described more specifically hereinafter, in respect of the present inventors' work involving heat shock protein (sHSP) and the truncated small heat shock protein (tsHSP) from the hyperthermophile *Pyrococcus furiosus*, as cloned and overexpressed in *E. coli*. The sHSP and tsHSP genes were found to be inducible by heat shock at 105° C. The present invention is effective at temperature from about 80° C. to about 110° C., and more preferably, from about 90° C. to about 100° C.

In a further aspect of the invention, the reagents described herein can be packaged in a kit form for carrying out PCR. As used herein, the term "package" refers to a solid matrix or materials customarily utilized in such a kit system in the form of at least one or more enclosure that is capable of holding within fixed limits at least one or more of the reagent components for use in PCR. Such materials include glass and plastic (e.g., polyethylene, polypropylene, and polycarbonate) bottle, vials, paper, plastic, plastic-foil laminated envelopes and the like. Thus, for example, a package can be a glass vial used to contain the appropriate quantities of polynucleotide primer(s), genomic DNA, vectors and DNA polymerase or a combination thereof, in addition to an appropriate amount of a heat shock protein, prefoldin and sHSP60 from *P. furiosus*. An aliquot of each component sufficient to perform at least one complete PCR procedure may be provided in each package.

Kits useful for producing a primer extension product for amplification of a specific nucleic acid sequence using a primer extension reaction methodology also typically includes, in separate container within the kit, dNTPs where N is adenine, thymine, guanine and cytosine and other like agents for performing primer extension reactions.

The reagent species of any system described herein can be provided in solution, as a liquid dispersion or as a substantively dry powder, e.g., the primers may be provided in lyophilized form.

The features and advantages of the invention are more fully apparent from the following illustrative examples, which are not intended in any way to be limitingly construed, as regards the invention hereinafter claimed.

EXAMPLES

Materials and Methods
Preparation of Recombinant Chaperones

*Pyrococcus furiosus* sHsp and Hsp60 were cloned, expressed and purified as previously described by Laksanalamai et al. and Emmerhoff et al., respectively (Emmerhoff et al. 1998; Laksanalamai et al. 2001). The genes encoding *P. furiosus* prefoldin alpha and beta subunits were identified based on the homology between the *P. furiosus* and *P. horikoshii* sequences (Okochi et at. 2002).

The prefoldin genes were amplified by PCR using the following primers:

```
Alpha prefoldin a:
5' primer,
                                          (SEQ ID NO: 6)
CCATATGGAAAACAATAAGGAATTgGAAAAGGTTGCT;

3', Primer,
                                          (SEQ ID NO: 7)
CCTCGAGTCACTTCTTAAGCTTGAAGCTCATTGCTTG, beta prefoldin:
5' primer
                                          (SEQ ID NO: 8)
CCATATGAATCCCAGGGTGTGCCAAGTGGATTTAGG
and 3' primer,
                                          (SEQ ID NO: 9)
CCTCGAGTCATCCAGCGGTTGGAGGTCTTAGGGCTGCCTGAATC.
```

The underlined letters indicate the restriction sites used for insertion. The PCR products were subsequently cloned into the expression vector, pET19b (Novagen) and transformed into BL21 competent cells (Novagen). The recombinant prefoldins were affinity purified on a nickel column (Ni-NTA, Qiagen) based on their N-terminal his-tags according to the product protocol.

Effect of the Small Heat Shock Protein on PCR Reactions

PCR reactions (45 ul final volume) were prepared as follows: IX Taq polymerase buffer (100 mM Tris-HCl, pH 9.0, 500 mM KCl and 15 mM $MgCl_2$), 1 mM dNTP, 1 uM each of forward and reverse primers, 20 nag of DNA template. A stock solution of Taq polymerase (5 U/ul, Cat: FB600030 Lot: 005975) was diluted five and ten fold to provide final concentrations of 0.025, 0.005 and 0.0025 U/ul in the PCR reactions. From a stock solution of a purified recombinant sHsp in Buffer A (25 mM potassium phosphate buffer, pH 7.0, 2 mM dithiothreitol and 1 mM EDTA) (Laksanalamai et al. 2001), sHsp was added to the PCR reaction providing a final concentration of 0.2 ug/ul. Control reactions without sHsp were performed with the addition of buffer A and water to adjust the total volume to 50 ul. The effect of sHsp on the concentration of Taq polymerase in the reaction mixtures was examined by PCR amplification with *P. furiosus* genomic DNA and a pair of primers that generate a 700 kb fragment.

Effect of Chaperones on Thermostability of Taq DNA Polymerase at 100° C.

Commercial Taq polymerase enzyme was diluted in 10 mM Tris-HCl pH 8.0 and 0.5 M NaCl to the final concentration of 0.5 U/ul in the presence of various combinations of the recombinant chaperones including individual subunits of prefoldin, prefoldin complex, Hsp60 and sHsp. Heat inactivation of the polymerase was carried out at 100° C. and the samples were removed at the indicated times. The residual activity of the polymerase was subsequently measured by quantitative primer extension assays. 25 ul mixtures were incubated in PTC-150 Monocycle (MJ.Research) at 100°. 3 ul samples were removed at defined times of incubation and assayed for primer extension activity. The primer-extension assay was performed with a fluorescent duplex substrate containing a primer-template junction (PTJ). The duplex was prepared by annealing a 5'-end labeled with fluoresce in 20-nt long primer with a 30-nt long template:

(SEQ ID NOs. 13 and 14)

```
FL-GTAATACGACTCACTATAGGG → extension
   |||||||||||||||||||||
   CATTATGCTGAGTGATATCCCAAAAACCCCC
```

DNA polymerase reaction mixtures (15 ul) contained dATP, dTTP, dCTP and dGTP (1 mM each), 4.5 mM $MgCl_2$, detergents Tween 20 and Nonidet P-40 (0.2% each), 0.2 uM PTJ, and appropriately diluted Taq polymerase. The primer extension was initiated by addition of the polymerase and carried out for 3 min at 70° C. in PTC-150 Minicycler (MJ Research). The extension products were applied on an ABI Prism 377 DNA sequencer (Applied BioSystems) and the fluorescent signals were analyzed as described in (Pavlov et al. 2002).

Results and Discussions

Taq DNA polymerase, an important enzyme in biotechnology (Dalton 1999; Dalton 2001; Pavlov et al. 2004), was used as a model substrate for examining the effects of chaperones on stability and durability of Taq polymerase, by incorporating chaperones into PCR reaction mixtures.

Enhancement of Taq Polymerase Performance in PCR Reactions by sHsp

The present inventor reported previously that the small heat shock protein (sHsp) from *Pyrococcus furiosus* (Pfu-sHsp) can prevent bovine glutamate dehydrogenase from aggregating at 50° C. (Laksanalamai et al 2001). During PCR reactions, the temperature fluctuates over a wide range, in this case, 50-95° C. Since the source of Taq polymerase is the thermophilic bacterium *Thermus aquaticus*, with a maximal growth temperature of 70° C. (Nold and Ward 1995), exposure to 95° C. can lead to the denaturation of Taq DNA polymerase during extended cycling. This experiment was performed based on the hypothesis that sHsp provides thermal stability by preventing precipitation of denatured Taq polymerase, thus, allowing the polymerase to undergo spontaneous refolding. To test this, decreased starting concentrations of Taq polymerase were used to establish conditions in which DNA amplification was limited by enzyme availability. The final concentrations of Taq polymerase are 0.025, 0.005 and 0.0025 U/ul in the reactions. Controls were identical reactions without the addition of sHsp.

Figure 1:
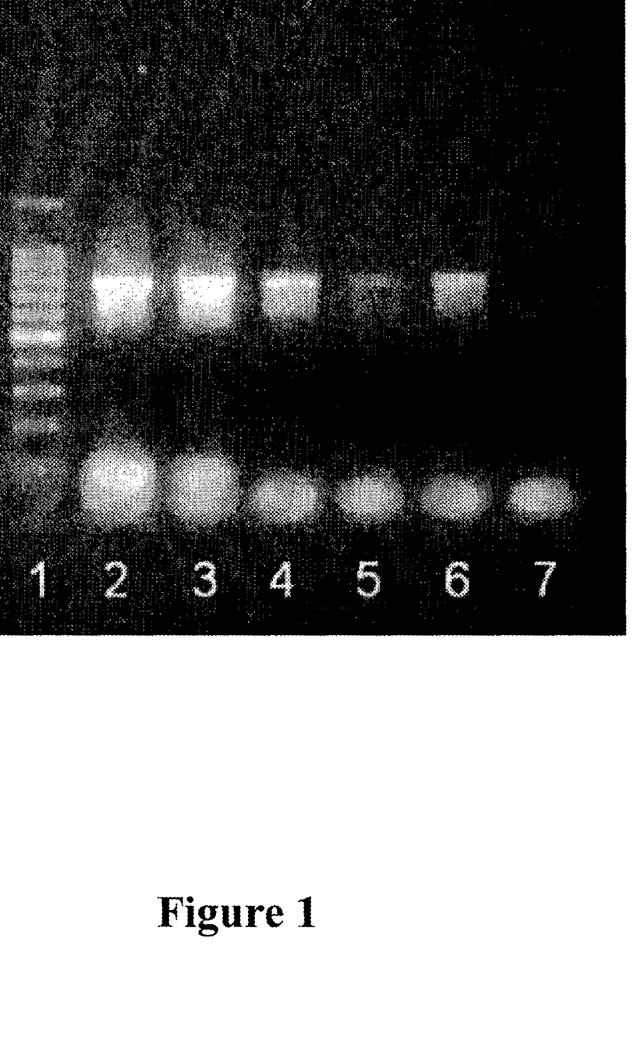
FIG. 1 shows the effect of sHsp from *P. furiosus* on Taq polymerase enzyme stability in PCR reactions. Lane 1 is a 100-bp DNA ladder. Lanes 2 and 3 are controls with non-diluted enzyme at 0.025 U/ul with and without sHsp, respectively. Lanes 4 and 5 are PCR products from reactions with 5-fold dilutions of Taq polymerase at 0.005 U/ul with and without sHsp, respectively. Lanes 6 and 7 are PCR products from reactions with 10-fold dilutions of Taq polymerase at 0.0025 U/ul with and without sHsp, respectively.

It was found that at a higher concentration of Taq polymerase (0.025 U/ul), PCR products are generated in both cases suggesting that sHsp does not interfere with the polymerase activity. Lower amounts of Taq polymerase molecules reduced the final amounts of PCR products visualized by gel electrophoresis (FIG. 1, lane 3 and 5) and that no detectable PCR products occurred in the PCR reaction with 0.0025 U/ul (FIG. 1, lane 7). With the addition of Pfu-sHsp, the level of PCR product was unaltered in the reactions with undiluted Taq polymerase and PCR products were still retained at 0.005 and 0.0025 U/ul of Taq polymerase (FIG. 1, lane 4 and 6, respectively). The visible PCR products in lanes 4 and 6 are convincing proof that Taq polymerase is extended by chaperone action. U.S. Pat. No. 6,579,703 and U.S. patent application Ser. No. 10/390,292, the contents of which are hereby incorporated by reference herein, describe the use of heat shock proteins and truncated versions that do not require an ATP hydrolysis and are able to function as efficient passive chaperones without interfering with the polymerase activity of its target protein. This function resembles the stabilizing action of alpha-crystallins, which perform similar functions in eye lenses. Unlike the alpha-crystallin, sHsps can function at very high temperature.

Since a single chaperone improved PCR reactions by reducing the amount of Taq polymerase required, the cooperative effects of several *P. furiosus* molecular chaperones were examined on the apparent thermostability of Taq polymerase quantitatively by means of primer extension assays followed by product quantitation as previously described by Pavlov et al. (Pavlov et al. 2002). Combinations of the chaperones were used in the experiments including sHsp, Hsp60, and prefoldins. Hsp60/sHsp and Hsp-prefoldin combinations were tested for their ability to stabilize Taq polymerase.

Stabilization of Taq Polymerase by a Combination of sHsp and Hsp60

Figure 2:
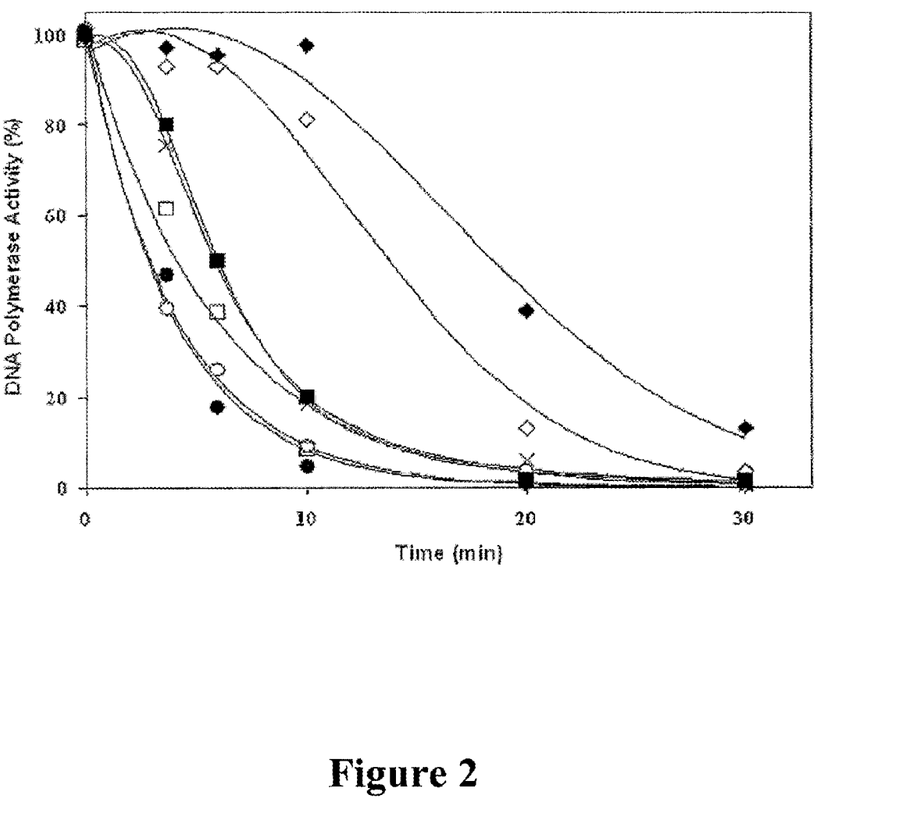
FIG. 2 shows the effect of chaperones on thermostability of Taq DNA polymerase in the presence of *P. furiosus* molecular chaperones (sHsp and Hsp60). Inactivation of Taq polymerase in the presence of individual subunits of sHsp (▽), Hsp60 (□), Hsp60-Mg2+-ATP(■), sHsp and HSP60 (◇) and sHsp and Hsp60-Mg2+-ATP(◆). The controls are reactions without the addition of chaperones (○) and with the addition of M2+ and ATP (●).

Since sHsps and Hsp60s are known to be passive and active protein chaperones respectively, it was theorized that sHsp retained denatured Taq polymerase in a soluble form and the soluble denatured proteins were subsequently refolded by Hsp60s. FIG. 2, open and closed circles, revealed that Taq polymerase was rapidly denatured at 100° C. and was reduced to less than 10% of the starting activity after 10 min of exposure to 100° C. with and without $Mg^{2+}$ and ATP. The combination of sHsp and Hsp60 was then used to study this hypothesis. The level of protection by the Hsp60 alone, FIG. 2, closed and open squares, was comparable to that of the sHsp alone (FIG. 2, crosses) and also consistent with the previous experiment. However, when both sHsp and Hsp60 were present without $Mg^{2+}$ and ATP, 80% of the initial polymerase activity was observed (FIG. 2, open diamonds) whereas 100% polymerase activity remained in the reaction at 10 min with the addition of $Mg^{2+}$ and ATP (FIG. 2, closed diamonds)

Stabilization of Taq Polymerase by a Combination of Prefoldin and Hsp60

Figure 3:
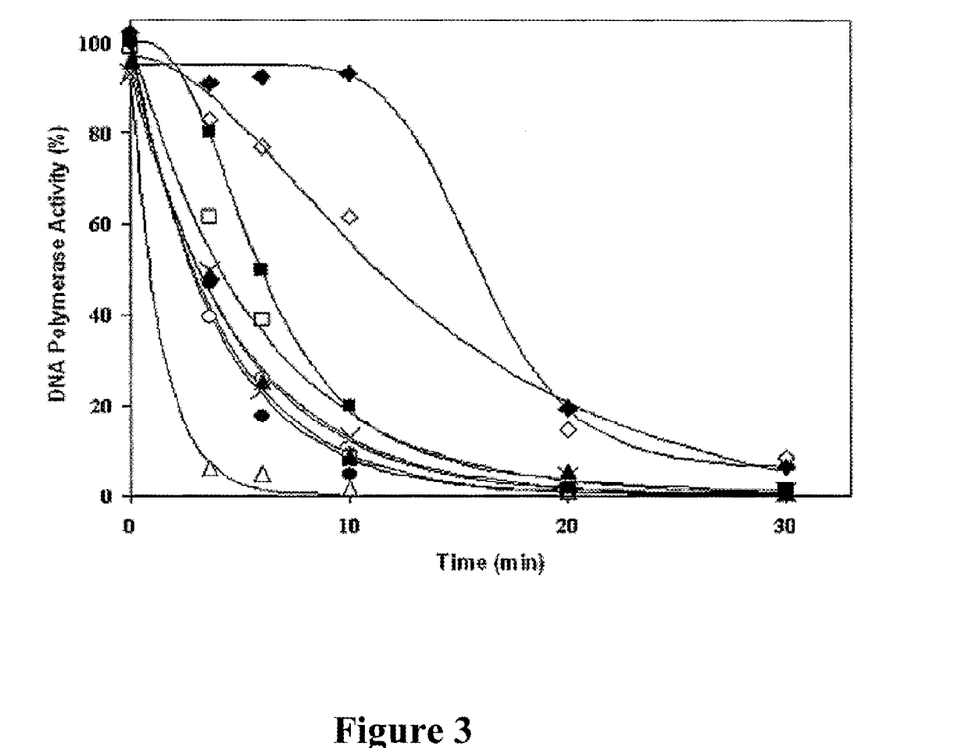
FIG. 3 shows the effect of chaperones on thermostability of Taq DNA polymerase in the presence of *P. furiosus* molecular chaperones (prefoldin and Hsp60). Inactivation of Taq polymerase in the presence of individual submits of prefoldin, prefoldin alpha (▽) and β (▼), prefoldin complex (X), Hsp60 (□), Hsp60-Mg2+-ATP (■), prefoldin and HSP60 (◇) and prefoldin and Hsp60-Mg2+-ATP (◆). The controls are reactions without the addition of chaperones (○) and with the addition of M2+ and ATP (●).

Since *P. furiosus* has two non-identical prefoldin subunits, the individual subunits of prefoldin (alpha and beta) were studied individually and the prefoldin complex. It was found that the levels of protection of Taq polymerase by prefoldin beta and prefoldin complex alone (FIG. 3, closed triangles and crosses) were comparable to those of the controls with the addition of $Mg^{2+}$ and ATP or without the addition of chaperones (FIG. 3, closed and open circles, respectively). Surprisingly, the addition of the prefoldin alpha destabilized the Taq polymerase (FIG. 3, open triangles) compared to the denaturation of Taq polymerase without chaperones presented (FIG. 3, open and closed circles). The Hsp60 alone caused a slight improvement of approximately 2 fold compared to controls (FIG. 3 closed and open squares, respectively). This effect occurred both with and without the addition of $Mg^{2+}$ and ATP. In the presence of the Hsp60 and prefoldin complex, 60% of the DNA polymerase activity was retained after 10 min at 100° C. without ATP (FIG. 3, open diamonds) whereas 95% of the polymerase activity was retained in the complete reaction with $Mg^{2+}$ and ATP (FIG. 3 closed diamonds).

The above-described results established that the *P. furiosus* chaperones in vitro can function together. It appears that co-chaperones such as prefoldin or sHsp are essential for optimal Hsp60 turnover as they facilitate its performance by five fold (FIGS. 2 and 3). Taq polymerase was used because it is a crucial enzyme in biotechnology applications such as PCR and cycle sequencing, as a model enzyme. This evidence indicates that chaperones from hyperthermophiles have potential applications in biotechnology. Using these chaperones from hyperthermophilic organisms could potentially improve a wide range of biotechnology applications demanding prolonged enzyme function at elevated temperatures.

In addition to these biotechnology applications, the present results could also define the protein folding pathways in *P. furiosus*. The present results indicated that prefoldins and sHsps have analogous roles as they both improve the efficiency of Hsp60 catalysis. Hsp60 and prefoldin subunits in *P. furiosus* are constitutively expressed (data not shown) whereas the sHsp is highly induced by heat shock treatment at 105° C. (Laksanalamai et al. 2001). In addition, after *P. furiosus* cells are removed from heat shock conditions and restored to growth conditions (95° C.), the levels of mRNA and protein appear to decrease rapidly as detected by Northern and Western blot, respectively (Laksanalamai, Lowe and Robb, unpublished results). This suggested that the co-chaperone functions of the prefoldins and Hsp60 may be sufficient for cells to contain protein folding problems at their normal growth temperature whereas elevated levels of sHsp may be required in addition to the prefoldins under heat shock conditions

REFERENCES

All references cited herein are incorporated herein by reference in their entirety and for all purposes to the same extent as if each individual publication or patent or patent application was specifically and individually indicated to be incorporated by reference in its entirety for all purposes.

Barral, J M, Broadley S A: Schaffar C, Hard F U. 2004. Roles of molecular chaperones in protein misfolding diseases. *Semin Cell Dev Biol* 15(1); 17-29.

Chang, Z, Primm, T P, Jakana J, Lee H I, Serysheva I, Chiu W, Gilbert H F, Quiocho F A. 1996. *Mycobacterium tuberculosis* 16-kDa antigen (Hsp16.3) functions as an oligomeric structure in vitro to suppress thermal aggregation *J Biol. Chem.* 271(12):7218-23.

Dalton, R., 1999. Roche's Taq patent 'obtained by deceit', rules U.S. court. *Nature* 402(6763):709.

Dalton, R., 2001. Patent ruling could cut PCR enzyme prices. *Nature* 411(6838):622.

Emmerhoff O J, Klenk H P, Birkeland N K. 1998. Characterization and sequence comparison of temperature-regulated chaperonins from the hyperthermophilic archacon *Archaeoglobus fulgiaus. Gene* 215(2):43 1-8.

Haley D A, Bova M P, Huang Q L, McHaourab H S, Stewart P L. 2000. Small heat-shock protein structures reveal a continuum from symmetric to variable assemblies. *J Mol Biol* 298(2):261-72.

Hartl F U. 1996. Molecular chaperones in cellular protein folding. *Nature* 381(6583)571-9.

Hartl, F U, Hayer-Hartl M. 2002. Molecular chaperones in the cytosol: from nascent chain to folded protein. *Science* 295 (5561): 1852-8.

Kim K K, Kim R, Kim S H. 1998. Crystal structure of a small heal-shock protein. *Nature* 394(6693):595-9.

Klunker D, Hlaas B., Hirtreiter A, Figueiredo L, Naylor D J, Pfeifer G, Muller V, Deppenmeier U, Gottschalk G, Hartl P U and others. 2003. Coexistence of group I and group II chaperonins in the archaeon *Methanosarcina mazei. J Biol Chem* 278(35) 3325&67.

Konicczny I, Liberek K. 2002. Cooperative action of *Escherichia coli* ClpB protein and DnaK chaperone in the activation of a replication initiation protein. *J Biol Chem* (21): 18483-8.

Laksanalamai P. Jiemjit A, Bu Z, Maeder D L, Robb F T. 2003. Multi-subunit assembly of the *Pyrococcus furiosus* small heat shock protein is essential for cellular protection at high temperature. *Extremophlies* 7(1):79-83.

Laksanalamai P., Maeder D L, Robb P T. 2001 Regulation and mechanism of action of the small heat shock protein from the hyperthermophilic archaeon *Pyrococcus furiosus*. *J Bacteriol* 183(17); S198-202.

Laksanalamai P, Whitehead T A, Robb F T 2004. Minimal protein-folding systems in hyperthermophilic archaea. *Nat Rev Microbiol* 2(4); 315-24.

Nold S C, Ward D M. 1995. Diverse Thermus species inhabit a single hot spring microbial mat. *Syst Appl Microbiol* 18:274-8.

Okochi M, Matsuzaki H, Nomura T, Ishii N, Yohda M. 2005. Molecular characterization of the group II chaperonin from the hyperthermophilic archaeum *Pyrococcus horikoshii* OT3. *Extremophiles* 9(2):127-34.

Okochi M, Nomura T, Zako T, Arakawa T, Iizuka R, Ueda H., Funatsu T, Leroux M, Yohda M. 2004. Kinetics and binding sites for interaction of prefoldin with group II chaperonin: contiguous non-native substrate and chaperonin binding sites in archaeal prefoldin. *J Biol. Chem*.

Okochi M, Yoshida T, Maruyama T, Kawarabayasi Y Kikuchi H, Yohda M. 2002. *Pyrococcus* prefoldin stabilizes protein-folding intermediates and transfers them to chaperonins for correct folding. *Biochem Biophys Res Commun* 291(4):769-74.

Pavlov A R, Belova G I Kozyavkin S A, Slesarev M. 2002. Helix-hairpin-helix motifs confer salt resistance and processivity on chimeric DNA polymerases. *Proc Natl Acad Sci USA* 99(21):13510-5.

Pavlov A R, Paviova N V, Kozyavkin S A, Slesarev A'. 2004. Recent developments in the optimization of thermostable DNA polymerases for efficient applications. *Trends Biotechnology* 22(s):253-60.

Robb P T, Maeder D L, Brown J R, DiRuggiero J, Stump M D, Yeh R K, Weiss R B, Dunn D M. 2001. Genomic sequence of hyperthermophile, *Pyrococcus furiosus*: implications for physiology and enzymology. *Methods Enzymol*. 330: 134-57.

van Montfort R L, Basha E, Friedrich K L, Slingsby C, Vierling F. 2001. Crystal structure and assembly of a eukaryotic small heat shock protein. *Nat Struct Biol*. 8(12): 1025-30.

Veinger L, Diamant S, Buchner J, Goloibompff P. 1998. The small heat-shock protein IbpB from *Escherichia coli* stabilizes stress-denatured proteins for subsequent refolding by a multi chaperone network. *J Biol Chem* 273(18):1 1032-7.

Yon J M. 2001. Protein folding: a perspective for biology, medicine and biotechnology. *Braz J Med Biol Res* 34(4): 419-35.

Young J C, Agashe V R, Siegers K, Hartl F U. 2004. Pathways of chaperone-mediated protein folding in the cytosol. *Nat Rev Mol Cell Biol* 5(10):781-91.

---

That which is claimed is:

1. A PCR amplification mixture comprising a recombinant DNA polymerase, a buffer solution and isolated proteins from *P. furiosus* consisting of a small heat shock protein (sHsp), prefoldin (Pfd) in combination with Hsp60, wherein all isolated proteins are from *P.furiosus* and are in an amount to enhance the stability of the recombinant DNA polymerase in the PCR amplification mixture, wherein the PCR amplification mixture is active at and has an elevated temperature of about 90° C. to about 100° C.

2. The PCR amplification mixture according to claim 1, wherein the prefoldin is a beta subunit.

3. The PCR amplification mixture according to claim 1, wherein the DNA polymerase is Taq polymerase.

4. The PCR amplification mixture according to claim 1, wherein the small heat shock protein comprises a sequence selected from (SEQ ID NO: 1), a truncated version thereof (SEQ ID NO: 2) or a homologous sequence have at least 90%, 95% or 99% homology thereof; wherein the subunit of prefoldin comprises a sequence selected from α subunit (SEQ ID NO: 3), αsubunit (SEQ ID NO: 4), a combination of both, or a homologous sequence have at least 90%, 95% or 99% homology thereof; and wherein the Hsp60 chaperonin comprises a sequence selected from (SEQ ID NO: 5) or a homologous sequence have at least 90%, 95% or 99% homology thereof.

* * * * *